United States Patent [19]
Kulkarni

[11] Patent Number: 6,066,754
[45] Date of Patent: May 23, 2000

[54] PROCESS FOR MANUFACTURING N-ALKOXY(OR ARYLOXY)CARBONYL ISOTHIOCYANATE DERIVATIVES USING N, N-DIALKYLARYLAMINE AS CATALYST

[75] Inventor: Shekhar V. Kulkarni, Shawnee, Kans.

[73] Assignee: Bayer Corporation, Pittsburgh, Pa.

[21] Appl. No.: 09/329,744

[22] Filed: Jun. 10, 1999

[51] Int. Cl.[7] .................... C07C 333/26; C07C 333/10; C07C 271/62; C07C 269/02
[52] U.S. Cl. ........................... 558/233; 560/16; 560/137; 560/148
[58] Field of Search ............... 558/233; 560/16, 560/137, 148

[56] References Cited

U.S. PATENT DOCUMENTS

| | | | |
|---|---|---|---|
| 4,659,853 | 4/1987 | Fu et al. | 558/233 X |
| 4,778,921 | 10/1988 | Lewellyn et al. | 560/137 |
| 5,194,673 | 3/1993 | Wang et al. | 560/137 |
| 5,728,729 | 3/1998 | Gayer et al. | 558/233 X |

OTHER PUBLICATIONS

Chem. Ber. 116, pp. 2044–2047 1983, Zur Kenntnis von Isothicyanaten der Thiokohlensäure–O–ester, Joachim Goerdeler und Werner Kunnes.

*Primary Examiner*—Michael G. Ambrose
*Attorney, Agent, or Firm*—Joseph C. Gil; Carol Marmo

[57] ABSTRACT

The present invention provides a process for making N-alkoxy(or aryloxy)carbonyl isothiocyanate derivatives by reacting a chloroformate with a thiocyanate, in the presence of an organic solvent and a catalytic amount of a N,N-dialkylarylamine, to produce a N-alkoxy(or aryloxy) carbonyl isothiocyanate intermediate product, wherein the intermediate product is converted to a N-alkoxy(or aryloxy) carbonyl isothiocyanate derivative in high yield and purity.

21 Claims, No Drawings

PROCESS FOR MANUFACTURING N-ALKOXY(OR ARYLOXY)CARBONYL ISOTHIOCYANATE DERIVATIVES USING N,N-DIALKYLARYLAMINE AS CATALYST

TECHNICAL FIELD OF THE INVENTION

The field of the present invention is the manufacture of carbonyl isothiocyanate derivatives. More particularly, the present invention pertains to an improved process for preparing N-alkoxy(or aryloxy)carbonyl isothiocyanate derivatives, wherein the improvement comprises the presence of a N,N-dialkylarylamine as a catalyst in the reaction process.

BACKGROUND OF THE INVENTION

Derivatives of carbonyl isothiocyanates are well known in the art, and various methods for their production are also known in the art.

U.S. Pat. No. 4,659,853 discloses a process for producing derivatives of alkoxy, aryloxy and alkene isothiocyanates by reacting a haloformate, an alkali, alkaline earth metal, lead or ammonium thiocyanate and a compound having the formula $R^1YH$ wherein $R^1$ is an alkyl, aryl or alkoxy, Y is oxygen, sulfur or $NR^2$ and $R^2$ is hydrogen or $R^1$, in the presence of a solvent or water and a catalyst. Suitable catalysts include pyridine, quinoline, pyrimidine, pyrazine, quinoxaline and the like.

U.S. Pat. No. 4,778,921 describes a process for the preparation of alkoxy and aryloxy isothiocyanates which includes the reaction of a haloformate and an alkali or alkaline earth metal thiocyanate in the presence of water and a catalyst. The catalyst comprises a six-membered mononuclear or ten-membered fused polynuclear aromatic, heterocyclic compound having one or two nitrogen atoms as the only hetero atoms in the ring.

U.S. Pat. No. 5,194,673 discloses a process for producing alkoxy and aryloxy isothiocyanates by the reaction of a haloformate and an alkali or alkaline earth metal thiocyanate in the presence of water and a catalyst. A co-catalyst is also used in the process to accelerate the reaction rate, increase product purity, and reduce the adverse effects of impurities in the thiocyanate reactants.

In the publication, Chem. Ber. 116, 2044, (1983), it is reported that the use of an aromatic heterocyclic nitrogen catalyst such as pyridine in carbon tetrachloride produced an alkoxythiocarbonyl isothiocyanate wherein the yield was only about 52%.

The most prevalent prior art methods comprise (i) the formation of the carbonyl isothiocyanate, (ii) the recovery and purification thereof, and (iii) the final reaction thereof with the appropriate co-reactant to produce the desired derivative. However, the known methods result in carbonyl isothiocyanate of low yield and purity. Thus, there is a need in the art for a process to produce carbonyl isothiocyanate derivatives in high yield and purity.

BRIEF SUMMARY OF INVENTION

The present invention provides a process for the preparation of N-alkoxy(or aryloxy)carbonyl isothiocyanate derivatives which includes reacting a chloroformate compound of the general formula (I)

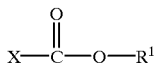

wherein $R^1$ represents a $C_1-C_8$ alkyl radical, a $C_2-C_4$ alkenyl radical, or a $C_6-C_{10}$ aryl radical; and X represents a halogen atom; with a thiocyanate of the general formula (II)

wherein M represents an alkali or alkaline earth metal, lead or $NH_4$, in the presence of an organic solvent, and in the presence of a catalytic amount of a N,N-dialkylarylamine of the general formula (III)

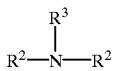

wherein $R^2$ each represents a $C_1-C_8$ alkyl radical or a $C_3-C_6$ alkenyl radical, or $R^2$ together represents a $C_5$ saturated heterocyclic ring or a $C_4$ saturated heterocyclic ring wherein O may be part of the ring; and $R^3$ represents an aryl group that can be a phenyl, a naphthyl, a substituted phenyl or a substituted naphthyl; to produce a N-alkoxy(or aryloxy) carbonyl isothiocyanate intermediate product of the general formula (IV)

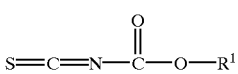

wherein $R^1$ is as defined above in formula (I); and reacting a compound of the general formula (V)

wherein $R^4$ represents a $C_1-C_{10}$ alkyl radical, a $C_6-C_{10}$ aryl radical, or a $C_1-C_8$ alkoxy radical, and Y represents oxygen, sulfur or $NR^5$, wherein $R^5$ represents hydrogen or $R^4$, with the intermediate product (IV) to produce a N-alkoxy(or aryloxy)carbonyl isothiocyanate derivative of the general formula (VI)

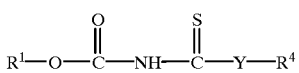

wherein $R^1$ is as defined above in formula (I), and $R^4$ and Y are as defined above in formula (V).

DETAILED DESCRIPTION OF THE INVENTION

The present invention provides a process for producing carbonyl isothiocyanate derivatives. In particular, the present process is used to produce N-alkoxy(or aryloxy) carbonyl isothiocyanate derivatives in high yield and purity. The process comprises reacting a chloroformate compound of the general formula (I)

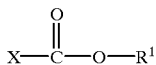
(I)

wherein $R^1$ represents a $C_1$–$C_8$ alkyl radical, a $C_2$–$C_4$ alkenyl radical or a $C_6$–$C_{10}$ aryl radical; and X represents a halogen atom, with a thiocyanate of the general formula (II)

MSCN (II)

wherein M represents an alkali or alkaline earth metal, lead, or $NH_4$, in the presence of an organic solvent, and in the presence of a catalytic amount of a N,N-dialkylarylamine of the general formula (III)

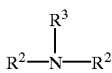
(III)

wherein $R^2$ each represents a $C_1$–$C_8$ alkyl radical or a $C_3$–$C_6$ alkenyl radical, or $R^2$ together represent a $C_5$ saturated heterocyclic ring or a $C_4$ saturated heterocyclic ring wherein O may be part of the ring; and $R^3$ represents an aryl group that can be a phenyl, a naphthyl, a substituted phenyl or a substituted naphthyl; to produce a N-alkoxy(or aryloxy) carbonyl isothiocyanate intermediate product of the general formula (IV)

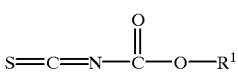
(IV)

wherein $R^1$ is as defined above in formula (I); and reacting a compound of the general formula (V)

$R^4$—Y—H (V)

wherein $R^4$ represents a $C_1$–$C_{10}$ alkyl radical, a $C_6$–$C_{10}$ aryl radical or a $C_1$–$C_8$ alkoxy radical, and Y represents oxygen, sulfur, or $NR^5$, wherein $R^5$ represents hydrogen or $R^4$, with the intermediate product (IV) to produce a N-alkoxy(or aryloxy)carbonyl isothiocyanate derivative of the general formula (VI)

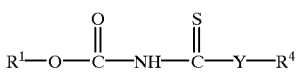
(VI)

wherein $R^1$ is as defined above in formula (I), and $R^4$ and Y are as defined above in formula (V).

The process of the present invention may be conducted in a one-pot process.

The process according to the invention is generally carried out at atmospheric pressure. The reaction of the chloroformate (formula I) with the thiocyanate (formula II) is carried out at a temperature of from about −10° C. to about 116° C.; and preferably at a temperature of from about 20 C. to about 40° C. The chloroformate is added to the reaction mixture at a rate such that the temperature of the reaction remains in the desired range. The reaction time for this step in the process of the invention is up to about 16 hours; and preferably the reaction time is from about 2 hours to about 4 hours. The progress of the reaction is monitored by liquid chromatography analysis of the reaction mixture to determine the amount of unreacted thiocyanate.

Suitable chloroformates for use in the process of the present invention include methyl, ethyl, propyl, isopropyl, butyl, isobutyl, amyl, hexyl, 2-ethylhexyl, benzyl, phenyl, and allyl chloroformates. In a preferred embodiment, the chloroformate is either methyl chloroformate or propyl chloroformate.

Suitable thiocyanates for use in the process of the present invention include metal, lead and ammonium thiocyanates. Suitable thiocyanates include sodium, lithium, potassium, rubidium, cesium, beryllium, magnesium, calcium, strontium, and barium thiocyanates. In a preferred embodiment, the thiocyanate is sodium thiocyanate.

The reaction of chloroformate and thiocyanate is carried out in the presence of a catalytic amount of a N,N-dialkylarylamine (formula II), and in the presence of an organic solvent.

Suitable N,N-dialkylarylamines for use as a catalyst in the reaction of the present invention include N,N-dimethylaniline, N,N-dimethyl-1-naphthylamine, N,N-dimethyl-p-toluidine, N,N-diethylaniline, N,N-diallylaniline, 1-phenylpiperidine and 4-phenylmorpholine. In a preferred embodiment, the N,N-dialkylarylamine catalyst is N,N-dimethylaniline. The amount of catalyst present in the reaction mixture is such that it comprises from about 0.1% to about 30% by mole based on the chloroformate; and preferably from about 3% to about 9% by mole.

Suitable solvents for use in the process of the present invention include organic solvents. Suitable organic solvents include alcohols such as methanol, ethanol, propanol, butanol; nitriles such as acetonitrile, propionitrile or butyronitrile; aromatic compounds such as benzene, toluene, xylene; halogenated hydrocarbons such as carbon tetrachloride; tetrahydrofuran; and ketones such as acetone or methyl isobutyl ketone. In a preferred embodiment, the solvent is methyl isobutyl ketone.

The reaction of the N-alkoxy(or aryloxy)carbonyl isothiocyanate intermediate product of formula IV with the compound of formula V is carried out at a temperature of from about −10° C. to about 116° C., and preferably from about 25° C. to about 50° C., for a time period of up to about 16 hours, and preferably from about 2 hours to about 4 hours.

Suitable compounds represented by formula V for use in the process of the present invention include alcohols such as methanol, ethanol, n-propyl alcohol, isopropyl alcohol, n-butyl alcohol, isobutyl alcohol, sec-butyl alcohol, amyl alcohols, hexyl alcohols, heptyl alcohols, cyclopentyl alcohol, cyclohexyl alcohol, allyl alcohols, benzyl alcohol; amines such as methylamine, ethylamine, hexylamine, isopropylamine, isobutylamine, amylamines, cyclohexylamine, octylamine, benzylamine, dimethylamine, diethylamine, dipropylamine, dibutylamine, diphenylamine, dibenzylamine, ethylmethylamine, N-methylaniline; mercaptans such as methyl mercaptan, ethyl mercaptan, propyl mercaptan, butyl mercaptan, amyl mercaptans, hexyl mercaptans, benzyl mercaptans, allyl mercaptans and the like. Preferred compounds of formula V are methanol and propanol.

In an embodiment of the present invention, following completion of the reaction between the N-alkoxy(or aryloxy)carbonyl isothiocyanate intermediate product and the compound of formula V, an acid such as aqueous hydrochloric acid or aqueous sulfuric acid may be added to the reaction mixture to neutralize the catalyst.

The invention is further illustrated but is not intended to be limited by the following examples in which all parts and percentages are by weight unless otherwise specified.

EXAMPLES

Example 1

8.3 grams (0.1 mole) of 98% pure sodium thiocyanate (NaSCN), 0.37 grams (0.003 mole) of the catalyst N,N-dimethylaniline, and 75 ml of methyl isobutyl ketone (MIBK) were charged to a reactor. The reaction mixture was stirred and heated to a temperature of about 85° C. The reaction mixture was made anhydrous by azeotropic distillation of a small amount of the solvent (about 20 ml) under a reduced pressure of about 200 mm of mercury. The reaction mixture was then cooled to room temperature under a nitrogen atmosphere. About 10.5 grams (0.11 mole) of 99% pure methyl chloroformate was added over a time period of about 30 minutes, maintaining the temperature of the reaction mixture between about 25° C. and about 40° C. The reaction mixture was then stirred for about 4 hours at room temperature to complete the formation of the intermediate N-methoxycarbonyl isothiocyanate To convert the MITC intermediate product to N-methoxycarbonyl-O-methyl thionocarbamate ("MTC"), 6.4 grams (0.20 mole) of methanol was added to the reaction mixture over a time period of about 15 minutes at room temperature. The mixture was then stirred at a temperature of about 50° C. for a time period of about 4 hours. The reaction mixture was then cooled to room temperature and the catalyst was neutralized by addition of a mixture of 30 ml of water and 3 ml of concentrated hydrochloric acid. The mixture was stirred for a period of about 15 minutes. The stirring was stopped, the mixture was allowed to settle, and the mixture separated into an organic phase and an aqueous phase. The organic phase (which contained the MTC product) was dried over anhydrous magnesium sulfate and the solvent was removed using a rotary evaporator at a temperature of about 50° C. to obtain 13.82 grams of crude MTC as residue. The purity of crude MTC was 98.9% (using liquid chromatography), which translated to a net yield of 91.7% based on the sodium thiocyanate.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of N-alkoxy(or aryloxy) carbonyl isothiocyanate derivatives comprising:

a) reacting a haloformate compound of the general formula (I)

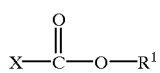  (I)

wherein $R^1$ represents a $C_1$–$C_8$ alkyl radical or a $C_2$–$C_4$ alkenyl radical, or a $C_6$–$C_{10}$ aryl radical, and X represents a halogen atom, with a thiocyanate of the general formula (II)

 (II)

wherein M represents an alkali or alkaline earth metal, lead or $NH_4$, in the presence of an organic solvent and in the presence of a catalytic amount of a N,N-dialkylarylamine of the general formula (III)

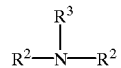 (III)

wherein $R^2$ each represents a $C_1$–$C_8$ alkyl radical or a $C_3$–$C_6$ alkenyl radical, or $R^2$ together represent a $C_5$ saturated heterocyclic ring or a $C_4$ saturated heterocyclic ring wherein O may be part of the ring; and $R^3$ represents an aryl group which is selected from a phenyl, a naphthyl, a substituted phenyl and a substituted naphthyl, to produce a N-alkoxy(or aryloxy)carbonyl isothiocyanate intermediate product of the general formula (IV)

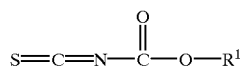 (IV)

wherein $R^1$ is as defined above in formula (I); and b) reacting the intermediate product (IV) with a compound of the general formula (V)

 (V)

wherein $R^4$ represents a $C_1$–$C_{10}$ alkyl radical, a $C_6$–$C_{10}$ aryl radical or a $C_1$–$C_8$ alkoxy radical, and Y represents oxygen, sulfur, or $NR^5$, wherein $R^5$ represents hydrogen or $R^4$, to produce a N-alkoxy(or aryloxy)carbonyl isothiocyanate derivative of the general formula (VI)

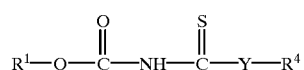 (VI)

wherein $R^1$ is as defined above in formula (I), and $R^4$ and Y are as defined above in formula (V).

2. The process of claim 1 wherein the chloroformate compound is selected from the group consisting of methyl, ethyl, propyl, isopropyl, butyl, isobutyl, amyl, hexyl, 2-ethylhexyl, benzyl, phenyl, and allyl chloroformates.

3. The process of claim 1 wherein the chloroformate compound is selected from the group consisting of methyl chloroformate and propyl chloroformate.

4. The process of claim 1 wherein the thiocyanate is selected from the group consisting of sodium, lithium, potassium, rubidium, cesium, beryllium, magnesium, calcium, strontium, and barium thioicyanates.

5. The process of claim 1 wherein the thiocyanate is sodium thiocyanate.

6. The process of claim 1 in step a) wherein the reaction is carried out at a temperature of from about −10° C. to about 116° C.

7. The process of claim 1 in step a) wherein the reaction is carried out at a temperature of from about 20° C. to about 40° C.

8. The process of claim 1 in step b) wherein the reaction is carried out at a temperature of from about −10° C. to about 116° C.

9. The process of claim 1 in step b) wherein the reaction is carried out at a temperature of from about 25° C. to about 50° C.

10. The process of claim 1 wherein the N,N-dialkylarylamine is selected from the group consisting of N,N-dimethylaniline, N,N-dimethyl-1-naphthylamine, N,N-dimethyl-p-toluidine, N,N-diethylaniline, N,N-diallylaniline, 1-phenylpiperidine, and 4-phenylmorpholine.

11. The process of claim 1 wherein the N,N-dialkylarylamine is N,N-dimethylaniline.

12. The process of claim 1 wherein the N,N-dialkylarylamine comprises from about 0.1% to about 30% by mole based on the chloroformate.

13. The process of claim 1 wherein the N,N-dialkylarylamine comprises from about 3% to about 9% by mole based on the chloroformate.

14. The process of claim 1 wherein the compound represented by formula V is selected from the group consisting of alcohols, amines and mercaptans.

15. The process of claim 1 wherein the compound represented by formula V is selected from the group consisting of methanol, ethanol, n-propyl alcohol, isopropyl alcohol, n-butyl alcohol, isobutyl alcohol, sec-butyl alcohol, amyl alcohols, hexyl alcohols, heptyl alcohols, cyclopentyl alcohol, cyclohexyl alcohol, allyl alcohols, benzyl alcohol, methylamine, ethylamine, hexylamine, isopropylamine, isobutylamine, amylamines, cyclohexylamine, octylamine, benzylamine, dimethylamine, diethylamine, dipropylamine, dibutylamine, diphenylamine, dibenzylamine, ethylmethylamine, N-methylaniline, methyl mercaptan, ethyl mercaptan, propyl mercaptan, butyl mercaptan, amyl mercaptans, hexyl mercaptans, benzyl mercaptans, and allyl mercaptans.

16. The process of claim 1 wherein the compound represented by formula V is selected from the group consisting of methanol and propanol.

17. The process of claim 1 wherein the organic solvent is selected from the group consisting of alcohols, nitriles, aromatic compounds, halogenated hydrocarbons, and ketones.

18. The process of claim 1, wherein the organic solvent is selected from the group consisting of methanol, ethanol, propanol, butanol, acetonitrile, propionitrile, butyronitrile, benzene, toluene, xylene, carbon tetrachloride, tetrahydrofuran, acetone, and methyl isobutyl ketone.

19. The process of claim 1, wherein the organic solvent is methyl isobutyl ketone.

20. The process of claim 1 in step b), further comprising the addition of an acid to the reaction mixture to neutralize the catalyst.

21. The process of claim 20, wherein the acid is selected from the group consisting of aqueous hydrochloric acid and aqueous sulfuric acid.

\* \* \* \* \*